United States Patent [19]

Wallshein

[11] 4,256,456
[45] Mar. 17, 1981

[54] TOOTH UPRIGHTING OR SEPARATING APPLIANCE

[76] Inventor: Melvin Wallshein, 8645 Bay Pkwy., Brooklyn, N.Y. 11214

[21] Appl. No.: 913,296

[22] Filed: Jun. 7, 1978

[51] Int. Cl.³ .............................................. A61C 7/00
[52] U.S. Cl. .................................................. 433/21
[58] Field of Search ................... 32/10 A; 132/89, 90; 24/137 A, 263 SB, 253, 253 R, 253 B; 267/154, 155, 158-165, 169; 433/148, 18, 21

[56] References Cited

U.S. PATENT DOCUMENTS

| | | | |
|---|---|---|---|
| 1,257,639 | 2/1918 | Rosenberger | 24/252 |
| 1,925,945 | 9/1933 | Zielinski et al. | 267/155 |
| 2,605,097 | 7/1952 | Masoner | 267/155 |
| 3,127,677 | 4/1964 | Schachter | 32/64 |
| 3,137,889 | 6/1964 | Sogoian | 267/164 |
| 3,414,976 | 12/1968 | Steiner | 32/14 A |

Primary Examiner—Robert Peshock
Attorney, Agent, or Firm—Frishauf, Holtz, Goodman & Woodward

[57] ABSTRACT

A tooth uprighting or separating appliance for cooperating with a pair of adjacent teeth having opposed and closely spaced side surfaces comprises a first member adapted to be interposed into a space between the pair of teeth for bearing against one of the opposed side surfaces of one of the pair of teeth, a second member adapted to be interposed into the space between the pair of teeth for bearing against the side surface of the other of the pair of teeth, and spring means interconnecting the first and second members for biassing the first and second members away from each other and toward the respective opposed side surfaces of the pair of teeth to thereby separate the teeth from each other. Preferably, the first and second members are adapted to pierce gum tissue which is located between the pair of teeth to facilitate installation. The spring means may comprise an elongated wire member or a coil spring portion from which the first and second means extend. The first and second members may both extend from the same side of the spring means, or may extend from opposite sides thereof.

47 Claims, 36 Drawing Figures

TOOTH UPRIGHTING OR SEPARATING APPLIANCE

This invention relates to tooth uprighters and separators which are particularly useful for uprighting impacted teeth and separating teeth in very close proximity.

Prior methods involve traumatic surgical techniques, or the use of auxiliary appliances which have a very limited tooth movement range. Other tooth uprighting and separating devices generally require one or more bands in the technique.

The object of this invention is to provide a simple but effective tooth uprighter and separator which is easy to manufacture, simple to use, has a large tooth movement range, requires no bands and which is medically effective with a minimum of pain and discomfort to the patient.

SUMMARY OF THE INVENTION

According to the present invention a tooth uprighting or separating appliance for cooperating with a pair of adjacent teeth having opposed and closely spaced side surfaces comprises a first member adapted to be interposed into a space between the pair of teeth for bearing against one of the opposed side surfaces of one of the pair of teeth, and a second member adapted to be interposed into the space between the pair of teeth for bearing against the side surface of the other of the pair of teeth. Spring means interconnects the first and second members of biassing the first and second members away from each other and toward the respective opposed side surfaces of the pair of teeth to thereby separate the teeth from each other. Preferably, the first and second members are adapted to pierce gum tissue which is located between the pair of teeth to facilitate installation.

The spring means may comprise an elongated wire member of a coil spring portion from which the first and second means extend. The first and second members may both extend from the same side of the spring means, or may extend from opposite sides thereof.

In preferred embodiments, the first and second members are generally "L" shaped or "C" shaped. In another preferred embodiment the first and second members are elongated plate-like members which are interconnected, preferably integrally connected, in their longitudinal direction, the connection area comprising the spring means.

DETAILED DESCRIPTION

Figure 1:
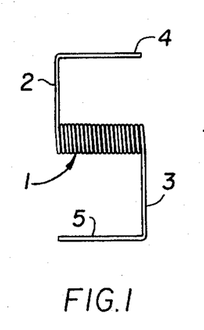
FIG. 1 illustrates an embodiment of the invention for use in spreading teeth, and in particular for uprighting impacted teeth.

Referring to FIG. 1, a tooth uprighter and separator according to the present invention comprises a coil spring portion 1, each end of the coil spring 1 terminating in respective legs 2, 3, the respective legs terminating in bent-over portions 4, 5, respectively. The relative dimensions of the legs, bent-over portions and coil spring portions in the embodiment of FIG. 1 are exemplary. The relative dimensions may be varied, depending upon the application of the device. Preferably, the spring portion 1, legs 2, 3 and bent-over portions 4, 5 are integrally formed. They could, however, be separated parts connected together, for example by welding.

Figure 2:
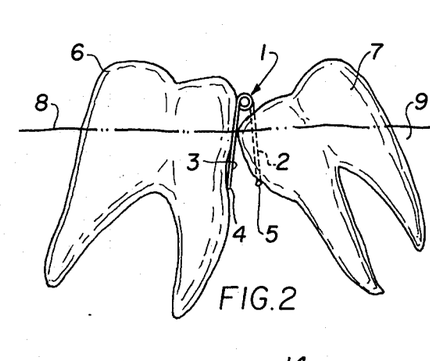
FIG. 2 illustrates the use of the device of FIG. 1 in uprighting an impacted tooth.

FIG. 2 illustrates a first application of the device for separating teeth 6 and 7. As shown in FIG. 2, the contact point between teeth 6 and 7 is approximately at the gum line 8. Tooth 7 can be considered to be impacted. The device of the present invention is installed by piercing the embrasure between the teeth 6, 7 and above the jawbone by means of one of the bent-over portion 4, 5 (for example 4), as seen in FIG. 2. The portions 4, 5 pierce the embrasure substantially transversely of the teeth; i.e., substantially perpendicular to the axial or height direction of the teeth. Completion of the installation is accomplished by orienting the spring portion 1 above the biting surfaces of the teeth and then orienting the leg on the opposite side (leg 3) for example along the inner side surface of the tooth and piercing the embrasure with the other bent-over portion 5 at a point below the contact point between teeth 6 and 7 with the bent-over portion 5 bearing against a side surface of tooth 6. The other bent-over portion 4 bears against a side surface of tooth 7 below the contact point between the teeth 6,7. In installing the device, in order to orient leg 2 relative to leg 3 as shown in FIG. 2, the legs are moved in such a direction so as to "wind" the spring 1 more tightly. After piercing the gum by bent-over portion 4, in order to insert the other bent-over portion 5 into the embrasure in the gum, after rotating or "winding" the spring 1 in a direction to tighten the spring, the leg 3 is pulled away from leg 2 in the axial direction of the spring 1 (by extending the spring) so as to displace leg 3 a sufficient distance from the side of the teeth to enable the bent-over portion 5 to be inserted into the embrasure by piercing same. The spring 1 may also be tilted up and away from the biting surfaces of the teeth to facilitate installation. Upon releasing the leg 3, the spring 1 pulls the leg 3 toward the leg 2 and due to the tendency of the spring to "unwind", bent-over portions 4 and 5 exert a separating force on the side walls of teeth 6 and 7 so as to cause tooth 7 to be uprighted and de-impacted.

The embodiment of FIG. 1 can also be operated to spread or upright a tooth which is completely below the gum line. In this instance, the complete device is buried within the gum. This may be done by piercing a hole in the gum above the bone and inserting the device in the resulting opening. Holes could also be drilled in the bone to receive the device. In extreme cases, appropriate incisions may be made by an orthodontist or dental surgeon to receive the tooth separating and uprighting device.

Figure 3:
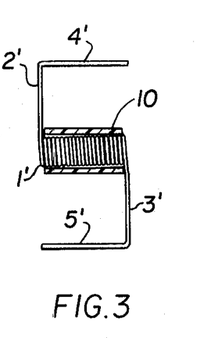
FIG. 3 illustrates a modification of the device of FIG. 1.

FIG. 3 illustrates a modified embodiment wherein the coil spring portion 1 is covered with a sleeve, for example made of plastic material. The sleeve is advantageous when the spring 1 is exposed in the mouth to prevent damage to the spring, damage to the teeth and mouth and to prevent food or other particles from becoming embedded in the spring. The sleeve also improves comfort to the patient. The sleeve may be made of a substantially white material to improve the esthetic value of the device. In FIG. 3, the sleeve 10 is shown partially in section for ease of illustration. In FIG. 3, the same reference numerals are used in FIG. 1, but with primes, are used for corresponding to elements. The device in FIG. 3 is shown having different relative dimensions than the device of FIG. 1, merely by way of example.

Figure 4:
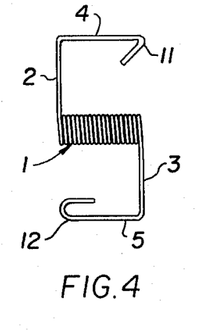
FIG. 4 illustrates a further modification of the device of FIG. 1.

FIG. 4 illustrates a further modified version of the device of FIG. 1 wherein the ends of the bent-over portions 4,5 are bent back on themselves. This improves the stability of the device in the mouth. By way of example, one leg 4 is shown with a generally V-shaped end portion 11 and the other bent-over portion 5 is shown with a generally U-shaped end portion 12. The bent-back portions of any single device preferably have the same shapes, and shapes other than those shown in FIG. 4 may be used. The bent-back portions 11,12 may be in any plane, i.e., in the plane of the paper in FIG. 4, perpendicular thereto, or at any angle thereto.

Figure 5:
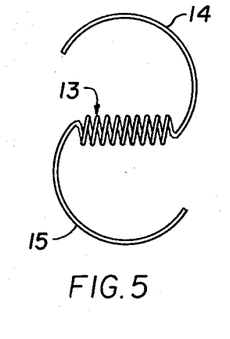
FIG. 5 illustrates a still further modification of the device of FIG. 1.

FIG. 5 illustrates a further modified embodiment wherein the device is generally "S-shaped". The substantially central coil spring portion 13 terminates in two curved legs 14, 15 at opposite ends thereof. The leg 14 is substantially equivalent in function to the combination of leg 2 and bent-over portion 4 of FIG. 1 and the leg 15 is substantially equivalent in function to a combination of the leg 3 and bent-over portion 5 of FIG. 1. The ends of legs 14 and 15 may be bent back on themselves, for example as shown at 11 and 12 in FIG. 4.

Figure 6:
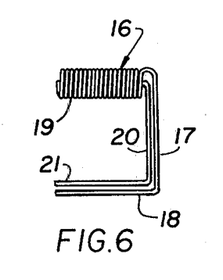
FIG. 6 illustrates another embodiment of the present invention.
Figure 7:
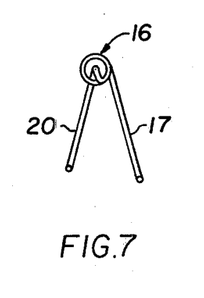
FIG. 7 is a side view of the embodiment of FIG. 6.
Figure 8:
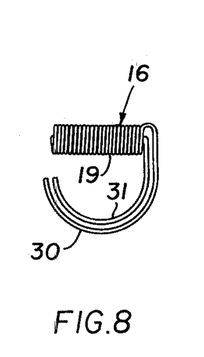
FIG. 8 illustrates a modified form of the embodiment of FIG. 6.

FIG. 6 illustrates a still further modification of the invention which is similar to that of FIG. 1, but which may be installed from only one side of the tooth. A coil spring 16 terminates in a first leg 17 which in turn terminates in a bent-over portion 18. The other end of the coil spring terminates in an integral portion 19 which passes back through the center of the coil spring 16 in the axial direction thereof. Axial member 19 terminates in a leg 20 on the same side of the spring as leg 17 and leg 20 in turn terminates in a bent-over portion 21. In the normal or rest condition, the legs 20 and 17 are springingly spread apart, for example as shown in the end view of FIG. 7. To install the device, the legs 17, 20 are brought together by "winding" the spring and the device is installed similarly to the device of FIG. 1 by piercing the gum or embrasure, with the bent-over portions 18, 21 bearing against the adjacent side surfaces of the teeth, in a manner similar to that of portions 4 and 5 in FIG. 2. The coil 16 is located above the contacting portion of the teeth, as also shown in FIG. 2. This embodiment has the advantage that the bent-over portions 18, 21 are inserted from only one side of the tooth, but has the disadvantage that it may be less stable in use than the devices illustrated in FIGS. 1–5. The ends of the bent-over portions 18, 21 may be bent back on themselves, for example as illustrated in FIG. 4. In the embodiment of FIGS. 6 and 7, additional springiness is provided by the torsion bar effect of axial member 19 when the legs 17,20 are brought together for installation in the mouth.

Figure 12:
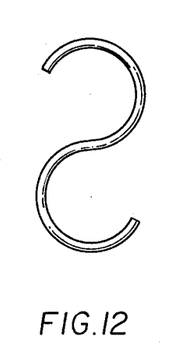

The embodiment of FIG. 6 may be modified to form the legs and bent over portions 17, 18 and 20, 21 so as to be curved, for example as shown by legs 30 and 31 in FIG. 12.

Figure 9:
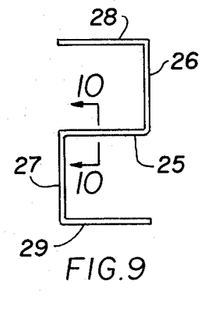
FIG. 9 illustrates still another embodiment of the invention made of rectangular or flat wire.
Figure 10:
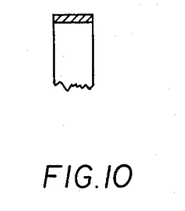
FIG. 10 is a cross-sectional view of the embodiment of FIG. 9 showing the cross-section of the wire used.

FIG. 9 illustrates a modified embodiment of the invention made of, for example rectangular or flat wire. In FIG. 9, the device comprises an elongated central portion 25 which terminates in legs 26, 27 at the opposite ends thereof, the respective legs terminating in bent over portions 28, 29, respectively. The wire from which the embodiment of FIG. 9 is preferably made is shown in cross-section in FIG. 10 as being rectangular or "flat" wire. In operation, when the legs 26, 27 are turned in substantial alignment with each other in order to be piercedly inserted into the gum or embrasure between two teeth, the axial portion 25 bends in torsion, tending to cause the legs 26, 27 to spring back toward the position shown in FIG. 9, thereby uprighting or separating the adjacent teeth. When the device of FIG. 9 is used as shown in FIG. 2, first one of the bent-over portions either 28 or 29 is inserted in the gum with the axial portion 25 being above the contacting point of the tooth, for example in a position similar to coil spring in FIG. 2. Then, the leg 28 is inserted by bending the leg 26 upwardly and away from the side surface of the tooth and generally deflecting bent-over portion 28 to insert same into the gum between the teeth. This arrangement is more difficult to install than the embodiment of FIGS. 1–8, but in some instance may be advantageous, and further is less expensive to fabricate than the embodiments of FIGS. 1–8. The device of FIG. 9 may have portions bent back on themselves at the end of the portions 28, 29 such as shown in FIG. 4. Moreover, in order not to have an exposed metal surface at the biting surface of the teeth, the axial portion 25 may be covered with a sleeve, for example as shown in FIG. 3. Still further, while the embodiment of FIG. 9 is shown fabricated from rectangular or flat wire, round or oval wire may be used.

Figure 11:
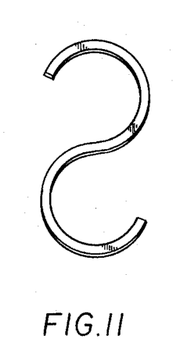
FIGS. 11 and 12 illustrate further embodiments of the invention.

The embodiment of FIG. 9 may be modified to take a generally S-shaped configuration as shown in FIG. 11. FIG. 11 illustrates the S-shaped version made from rectangular or flat wire. The operation thereof is similar to the embodiment of FIG. 9. In FIG. 12 the S-shaped version is shown fabricated from a round wire.

Figures 13, 14:
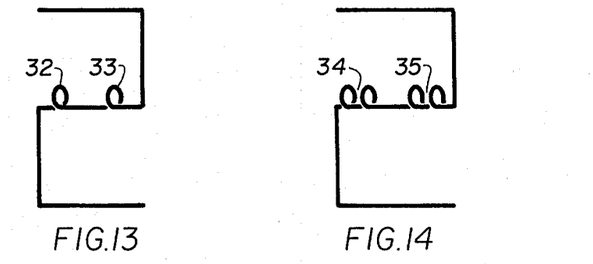
FIGS. 13 and 14 illustrate modifications of the embodiment of FIG. 9.

FIG. 13, illustrated in line drawing, is an embodiment similar to FIG. 9, but wherein the wire is bent in two places to form springs 32, 33. The springs 32, 33 are single-turn spring portions but may be multi-turn spring portions 34, 35 as illustrated in FIG. 14. The spring portions 32–35 in FIGS. 13 and 14 improve the resiliency of the device and aid in facilitating installation. They also improve the spring-effect of the device in some applications. The device of FIGS. 13 and 14 is installed in the mouth similarly to the device of FIG. 9.

The spring portions 32–35 may be flat coils which lie in the plane of the paper in FIGS. 13 and 14, but may be perpendicular to the paper or in any other direction relative to the remainder of the device. The embodiments of FIGS. 13 and 14 are illustrated in a single-line representation of the wire. The wire from which the device is made may be rectangular, round, oval or in any other desired cross-sectional shape. Additionally, the springs 32–35 may be added to the embodiments of FIGS. 11 and 12, as desired. Still further, the number of spring portions formed in the embodiments of FIGS. 11–14 may be two (as shown in FIG. 13) or any other number. For example, only one spring portion in the central portion of leg 25 (FIG. 9) may be formed.

Figure 15:
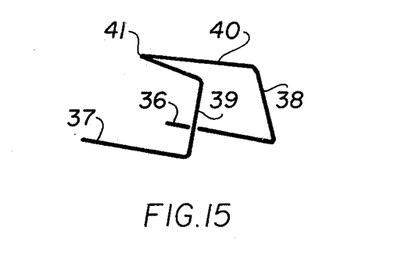
FIGS. 15 and 16 illustrate further embodiments of the invention.
Figure 16:
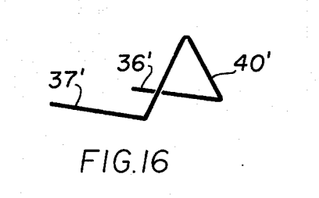

FIG. 15 and 16 illustrate further embodiments of the invention which are preferably fabricated from an integral piece of wire. Again, these embodiments are illustrated in single-line format, but the wire may take any desired cross-sectional shape.

Referring to FIG. 15, the device comprises first and second legs 36, 37 which are adapted to bear against the side surfaces of two adjacent teeth, similar to portions 4 and 5 of the embodiment of FIG. 1. Extending from legs 36, 37 are substantially upright portions 38, 39 which extend into a generally V-shaped joining portion 40. In use, the device is installed in the mouth by piercing the gum or embrasure with legs 36, 37 so that these legs bear against the side walls of the teeth. In order to install the device in this manner, the upright portions 38, 39 are squeezed together so as to bring legs 36, 37 closer to each other. The joining portion 40 overlies the biting surface of the teeth or, if possible, lies in the joining area similar to portion 1 shown in FIG. 2. If desired, the joining portion 40 may be fabricated long enough so as to extend completely over the top surface of the teeth and have its apex portion 41 bent downwardly over the side of the tooth opposite upright portions 38, 39 to more securely lock the device in position.

Figure 17:
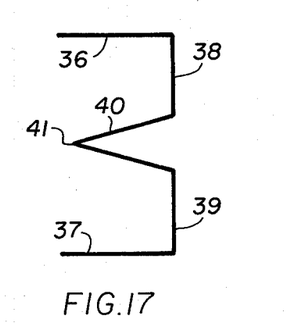
FIGS. 17 and 18 illustrates the embodiment of FIGS. 15 and 16, respectively, in the flat, inactive form.
Figure 18:
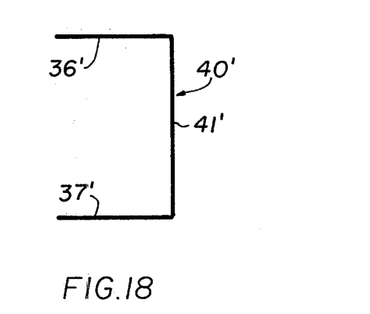

FIG. 16 illustrates an embodiment wherein legs 36', 37' are joined by an upright joining portion 40' which does not extend over the top surfaces of the teeth. The legs 36', 37' can be made long enough so as to extend outward through the side of the gum opposite joining portion 40' so as to be bent upwardly, outwardly, etc. to help retain the device in position. The devices of FIGS. 15 and 16 operate similarly to those of FIGS. 6–8. In FIGS. 15 and 16, the devices are shown in the positions almost ready for insertion between a pair of teeth. In practice, the devices may be fabricated from a wire in a flat form and may be "sprung" by the user into the condition shown in FIGS. 15 and 16 for installation in the mouth. For example, the embodiment of FIG. 15, in the flat state, may look substantially as shown in FIG. 17 and the embodiment of FIG. 16 may look substantially as shown in FIG. 18. As shown in FIG. 18, the apex of joining portion 40' may be slightly scored so as to insure that the wire will properly bend in use.

Figure 19:
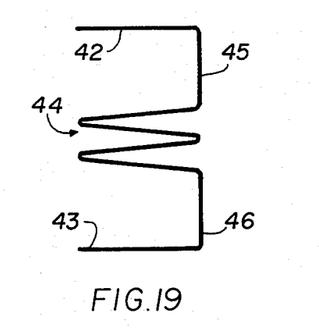
FIG. 19 illustrates a modification of the embodiment of FIG. 15.

FIG. 19 illustrates a modification to the embodiment of FIGS. 15 and 17. The legs 42, 43 are similar to the legs 36, 37 and the generally "M" shaped joining portion 44 serves substantially the same function as joining portion 40. The device is deformed for use so as to take a shape substantially similar to that shown in FIG. 15, the leg portions 45, 46 in FIG. 19 corresponding to the leg portions 38, 39, respectively, in FIG. 15. Since the joining portion 44 is more tortuous in the embodiment of FIG. 19, a different spring-characteristic is obtained. By varying the shape and size of the joining portion 44, different spring characteristics can be provided.

Figure 20:
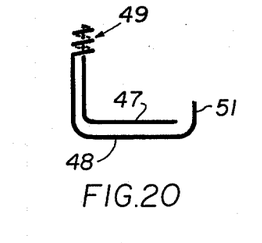
FIGS. 20–23 illustrate further embodiments of the invention using different types of spring means.
Figure 21:
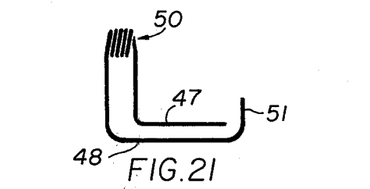
Figures 22, 23:
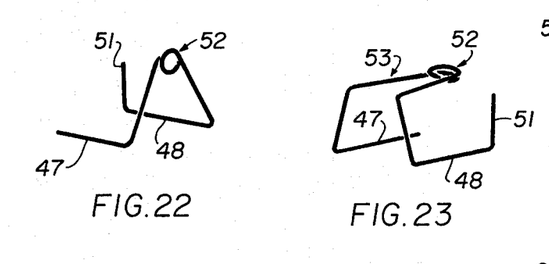

FIGS. 20 and 21 illustrate further embodiments of the invention wherein legs 47, 48 are joined by a spring portion to bias the legs apart from each other, one of the legs 48 having an upwardly extending portion 51 which extends through the opposite side of the gum to help stabilize the device in the mouth and to keep it securely located. In FIG. 20, the spring 49 is a coil spring having generally horizontally arranged turns, whereas the spring 50 joining the legs 47, 48 in FIG. 21 has generally vertically arranged turns. The springs 49, 50 may be single-turn or multi-turn springs, as desired. The springs 49, 50 may be formed in other planes as well as those shown in FIGS. 20 and 21, for example as shown by spring 52 in FIG. 22. In FIGS. 20–22, the legs 47, 48 are generally relatively far apart when the device is in its inactive state, the legs being pressed toward each other against the spring force for installation in the mouth by piercing the gums by legs 47, 48.

The coil spring portion may form the end of a joining portion 53, as shown in FIG. 23, so that the spring 52 of FIG. 23 lies over the top surface of the teeth being separated or uprighted. Other than the provision of the substantially horizontally directed joining portion 53, the embodiment of FIG. 23 is essentially similar to that of FIG. 22.

Figure 24:
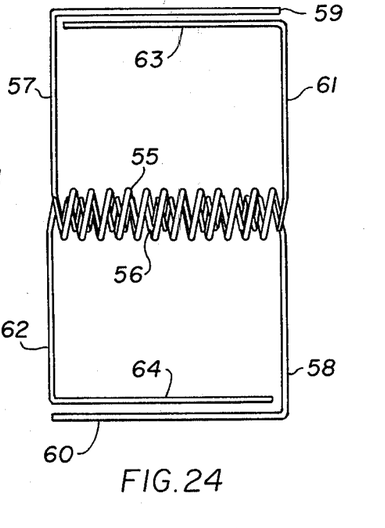
FIG. 24 illustrates an embodiment modified from that of FIG. 1 utilizing nested spring means.

Shown in enlarged form in FIG. 24 is a further modification of the invention which essentially comprises two devices similar to that of FIG. 1 in nested configuration. The coil springs 56 are shown in FIG. 24 as having widely separated turns. In practice, however, the coils 55, 56 are preferably tightly wound with adjacent abutting or almost abutting turns. The outer coil spring 55 terminates in opposite legs 57, 58 which in turn terminate in respective bent-over portions 59, 60. Coil spring 56, which is located within the lumen of coil spring 55, terminates in respective legs 61, 62 which in turn terminate in respective bent-over portions 63, 64, respectively. The device of FIG. 24 is installed in a similar manner as the device of FIG. 1, for example by piercing the gum or embrasure by means of the ends of bent-over portions 59, 60, 63, 64. By virtue of the provision of springs 56, 57, after insertion of one of the bent-over portions of each spring between the teeth, the opposite bent-over portions may be sprung into position for piercing the gum by bending and/or extending the respective coil spring along its axial length. The embodiment of FIG. 24 is more symmetrical in nature and should provide a more stable device which maintains itself more securely and positively in the mouth. Moreover, since two springs are employed, higher forces are obtained.

Other nested spring arrangements could be used in place of the arrangement shown in FIG. 24. For example, two devices such as shown in FIGS. 13 and 14 may be used together, the devices being directed opposite with respect to each other and with their coil springs preferably nested or otherwise interengaged with each other to improve stability. The coil springs of the FIG. 24 embodiment may have interleaved turns rather than one spring being nested with the other.

Figure 25:
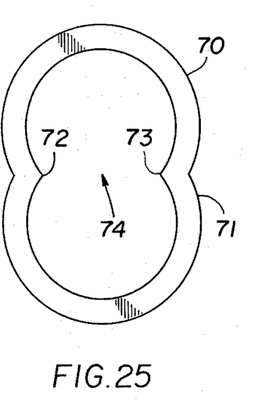
FIGS. 25 and 26 illustrate yet another embodiment of the invention.

FIG. 25 illustrates another embodiment of the invention wherein the device is a generally figure-8 form (with the central portion thereof open) which is comprised of an upper open circular portion 7 and a lower open circular portion 71, preferably integrally formed with each other. The device is preferably fabricated in the flat form as shown in FIG. 25 of wire (of desired cross-sectional configuration such as round, oval, rectangular, etc.), flat spring metal material or of plastic material.

Figure 26:
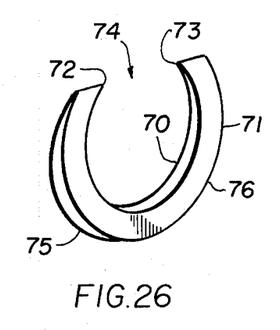

In use, the open circular portions 70,71 are folded back on each other, as shown in FIG. 26. The generally pointed joining portions 72,73 of the open circular portions 70,71 serve as piercing parts for installation of the device in the mouth between two adjacent teeth. For example, the device is installed by keeping the open circular portions in the together position shown in FIG. 26 and the gum of embrasure is pierced by one of the pointed piercing portions 72,73 at a point below the contact point between the two teeth which are to be separated and the device is rotated around such that the open area 74 is now adjacent the biting surface of the teeth and the closed areas 75,76 bear aagainst the side surfaces of the teeth, similar to bent-over portions 4,5 of FIG. 2 to exert a separating force to the teeth. The separating force is achieved by virtue of the springiness of the material from which the device is made which is developed when the open loop portions 70,71 are bent back on themselves as shown in FIG. 26. The springiness of the material provides the biasing force which separates or uprights the teeth.

If desired, loops may be formed in the material at the joining points 72,73 to change the spring-characteristics of the material in use.

Figure 27:
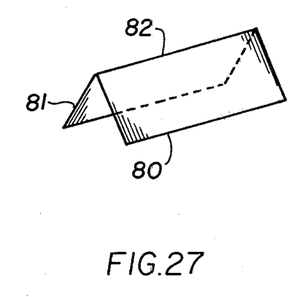
FIGS. 27 and 28 illustrate still a further embodiment of the invention.
Figure 28:
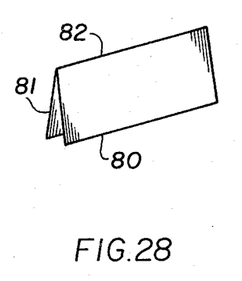
Figure 29:
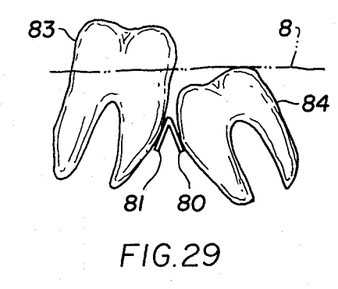
FIG. 29 illustrates the embodiment of FIGS. 27 and 28 in use between teeth.

FIG. 27 illustrates another embodiment of the invention fabricated from elongated flat members 80,81 joined at 82. The device of FIG. 27 may be fabricated of metal or plastic material. The device may be fabricated to take the form shown in FIG. 27 in the rest condition, or may be flat with the flat portions 80, 81 in the same plane. When fabricated flat, the joining portion 82 is scored, or the like, to insure that the device folds or bends properly during use. To install the device, the elongated flat members 80,81 are folded toward each other, for example as shown in FIG. 27, by means of pliers, or the like, and is then inserted directly into the embrasure. The complete device is inserted into the embrasure below the contact point of the teeth, for example as shown in FIG. 29. In FIG. 29, tooth 83 extends above the gum line 8 and the other tooth 84 is completely impacted. The device of FIGS. 27 and 28 is inserted between the teeth and operates as shown in FIG. 29. The tendency of the flat portions 80,81 to spring apart imparts uprighting forces to the side surface of tooth 84, thereby causing same to erupt above the gum line in due course. If there is insufficient embrasure below the contact point, the device is installed in a hole which is either pierced or drilled by the orthodontist or surgeon. The device could be used for partially impacted teeth, for example as shown in FIG. 2, or for non-impacted teeth (not shown).

The devices of FIGS. 27 and 28 are preferably made of flat spring metal material, but also may be made of resilient plastic material.

Figure 30:
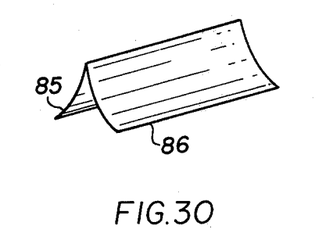
FIG. 30 illustrates a modified form of the embodiment of FIGS. 27 and 28.

FIG. 30 illustrates a modification of the device of FIGS. 27 and 28. In FIG. 30, the flat elongated members 80,81 are replaced by elongated members 85,86 which are curved as illustrated in FIG. 30. The curvatures of the members 85,86 are merely exemplary-other curvatures could be used, as desired.

Figure 31:
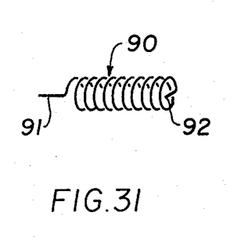
FIGS. 31–33 illustrate further embodiments of the invention.

FIG. 31 illustrates another embodiment of the invention which comprises a coil spring 90 having first and second ends 91,92. The spring 90 is shown in FIG. 31 in its sprung or open condition. In use, the spring 90 is wound or tightened so that its cross-sectional diameter is substantially reduced to a sufficient degree that it may fit completely into the space between the teeth which are to be separated. For example, referring to FIG. 2, the spring 90 is wound or tightened so that it may fit in the space between the teeth below the contact point between the two teeth. After insertion between the teeth, the spring is released so that it tends to unwind, thereby generating opposing oppositely directed forces on the facing side surfaces of the adjacent teeth.

Figure 32:
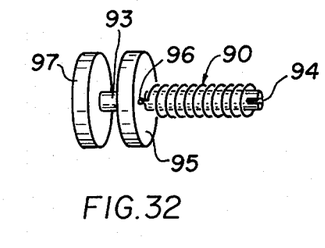

FIG. 23 illustrates a tool for use in winding the spring 90. The tool comprises a shaft 93 having a slot 94 in the end thereof for receiving the end portion 92 of the spring. Mounted on shaft 93 is a rotatable collar 95 having an opening 96 therein for receiving the other end 91 of the spring. A manipulating member or key 97 is provided at the end of shaft 93. To use the tool, the spring is engaged with the tool as shown in FIG. 32 and the shaft 93 is rotated relative to the collar 95 so as to wind the spring to reduce the diameter of the spring 90. After winding, the spring 90 is inserted into the space between the teeth and the collar 95 and shaft 93 are released, thereby permitting the spring to tend to unwind and increase its diameter. The tool may be left in place in the mouth, or may be removed by merely pulling same out to the left as seen in FIG. 32.

Figure 33:
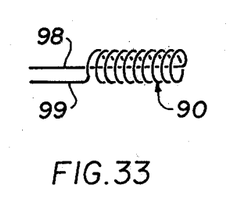

FIG. 33 illustrates a modification to the embodiment of FIG. 31. In FIG. 33, the spring 90 has an elongated end 98 which passes through the lumen of the spring from one end to the other. The other end 99 of the spring extends in a spaced manner from the first end 98. To wind the spring, the user merely grips the end 98, for example with pliers, and winds the end 99 in a direction to tighten or reduce the diameter of the spring 90. When the spring is wound, it is inserted in the mouth in a manner similar to the spring of FIG. 31 and legs 98 and 99 are released, thereby permitting the spring 90 to tend to unwind or expand, to create separating forces against the opposing surfaces of the teeth.

Figures 34, 35:
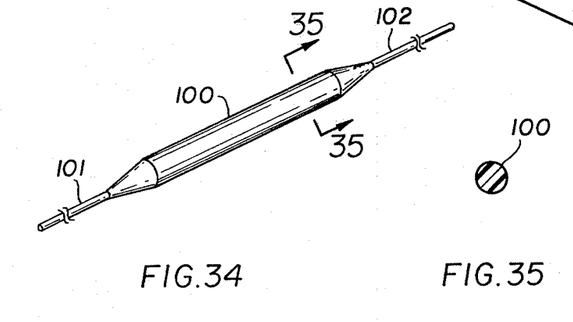
FIGS. 34–36 illustrate still further embodiments of the invention.

FIG. 34 illustrates a further embodiment of the invention which is made purely of elastomeric material. The embodiment comprises a body section 100 which may be wound in cross-section as seen in FIG. 35 or any other shape. Extending from the body portion 100 of the device are relatively thin end sections 101, 102 which function to pass through a small space between the teeth to be separated so that the user can stretch the body 100 to reduce its cross-sectional dimensions to squeeze same through the space between the teeth, at which point the pulling forces on end members 101,102 are released. Upon release of members 101,102, the body portion 100 tends to return to its original larger cross-sectional shape, thereby exerting separating forces against the opposing side surfaces of the teeth. The embodiment of FIG. 34 is used in a similar manner as the embodiments of FIGS. 31-33 and is inserted in substantially the same area between the teeth. If gum tissue blocks the access to the space between the teeth, then a hole is merely pierced through the gum tissue by a sharp object and one of the end members 101,102 is threaded through the hole for installation of the device. The body portion 100 and end members 101,102 are preferably integrally formed with the end members tapering down from the body member 100 for improved strength.

Figure 36:
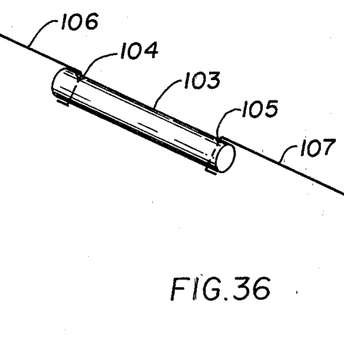

FIG. 36 illustrates a further embodiment of the invention which operates similarly to that of FIG. 34. The body member 103, which may be round in cross-section or any other shape, has through holes 104,105 adjacent the ends thereof for receiving installation members 106,107. Installation members 106,107 may be elongated pieces of wire or any other dental implement having a hook at the end thereof to engage the holes 104,105. The wire or other rigid dental implement engaging holes 104,105 may serve the dual purpose of acting as a piercing member for the gum tissue between the teeth. The installation of the embodiment of FIG. 36 is similar to that of FIG. 34. After installation, the end members 106,107 in FIG. 36 are removed, and the end members 101,102 of FIG. 34 are cut off.

The body members 100 and 103 of FIGS. 34 and 36, respectively, may be made from any suitable elastomeric material, such as polyurethane. Other suitable materials resistant to mouth fluids and foods can be used.

The tooth uprighting or separating appliances of the present invention, except for the embodiment of FIGS. 28-30, are preferably made of metallic wire which is resilient. Stainless steel wire is particularly suitable and typical stainless steel wires which may be used are 302, 304, 17-7 wires. When the devices are fabricated of round wires, typical wire diameters may range from 0.010–0.016 inches, although other wire sizes may be used, as desired. Other wire cross-sectional shapes may also be used, such as rectangular, round, oval or any other desired shape. Many of the embodiments may also be made of flat spring metal material, such as the embodiments of FIGS. 9-11, 17-19 and 25-30. The coil springs shown in FIGS. 1, 3, 4, 6, 8 and 24 are preferably more tightly wound than shown in the drawings. The drawings illustrate the springs as more loosely wound for ease of illustration. In FIGS. 20-23, upwardly turned members 51 are provided to more securely retain the appliance in place when mounted between teeth. Similar upwardly turned portions may be provided on the other legs 47, or the upwardly turned portions 51 may be omitted.

While the illustration in FIG. 2 is shown with a partially impacted tooth, it should be clear that any of the embodiments of the invention may be used in the fully impacted tooth configuration illustrated in FIG. 29. If there is insufficient embrasure below the contact point of the teeth, then a hole is either pierced or drilled in the gum or bone below the contact point and a device according to the present invention is accordingly inserted between the teeth to exert the appropriate forces to separate the teeth or upright at least one of the teeth.

The portions of the various devices of the invention which are adapted to pierce the gum or embrasure may have pointed or other suitably shaped surface configurations to facilitate the piercing operation. Moreover, the ends of any of the embodiments of the invention, except for those of FIGS. 25-30, may have bent-back portions, similar to portions 11 and 12 of FIG. 4 to stabilize the members in use. The bent-back portions, for example such as portions 11, 12, are suitably shaped such that piercing of the gum or embrasure may still be performed without difficulty. Still further, sleeves, similar to sleeve 10 in FIG. 3, may be provided on any of the portions of the appliances of the present invention which are to be exposed in the mouth, for example for esthetic purposes or for protection to the appliance and/or the teeth which may bear against the appliance during chewing, for example the opposing teeth. Where the appliances are of the type which are formed by wire, it should be clear that any type of suitably resilient wire of desired cross-sectional shape may be used, or resilient plastic materials of suitable strength may be used.

I claim:

1. A self-retaining tooth uprighting or separating appliance for cooperating with a pair of adjacent teeth having opposing and closely spaced side surfaces, comprising:

first means adapted to be interposed into a space between said pair of teeth for bearing against one of said opposing side surfaces of one of said pair of teeth;

second means adapted to be interposed into the space between said pair of teeth for bearing against said side surface of the other of said pair of teeth which is opposed to said side surface against which said first means bears;

spring means interconnecting said first and second means and biassing said first and second means away from each other and toward said respective opposed side surfaces of said pair of teeth to separate said pair of teeth, said spring means also applying an uplifting force to at least one of said first and second means relative to the other of said first and second means, and said spring means having a dimension in the widthwise or buccal direction of a tooth which is not substantially greater than the width of a tooth, and said spring means having a further dimension in the lengthwise direction of a tooth which is not greater than the height of the crown of the tooth; and cooperating engagement means on each of said first and second means for directly contacting said engaging said respective side surfaces of said adjacent teeth to prevent disengagement of said appliance from said adjacent teeth to prevent disengagement of said appliance from said adjacent teeth without requiring external anchoring devices, the appliance thereby being self-retaining relative to said adjacent teeth.

2. The appliance of claim 1 wherein said first and second means comprise means for piercing gum tissue which is located between said pair of teeth, and for locating said cooperating engagement means in said gum tissue.

3. The appliance of claim 1 wherein said spring means is adapted to be located at or above the biting surface of said pair of teeth.

4. The appliance of any one of claims 1-3 wherein said spring means comprises an elongated coil spring.

5. The appliance of claim 4 further comprising a sleeve mounted around said elongated coil spring.

6. The appliance of claim 5 wherein said sleeve is made of resilient material.

7. The appliance of claim 1 wherein said first and second means each comprises generally L-shaped members, one leg of each of said L-shaped members extending from said spring means and the other legs thereof being adapted to be inserted between said teeth so as to bear upon said respective opposed side surfaces of said pair of teeth, said other legs comprising said cooperating engagement means.

8. The appliance of claim 1, wherein each of said first and second means each comprise generally C-shaped members, one end of each of said C-shaped members extending from said spring means and the other ends thereof being adapted to be inserted between said teeth so as to bear upon said respective opposed side surfaces of said pair of teeth, said other ends comprising said cooperating engagement means.

9. The appliance of claim 8, wherein said appliance is generally S-shaped.

10. The appliance of either of claims 7 or 8, wherein said first and second means extend from said spring means on the same side of said spring means.

11. The appliance of either of claims 7 or 8, wherein said first and second means extend from said spring means on opposite sides of said spring means.

12. The appliance of either of claims 1 or 2, wherein said spring means comprises an elongated coil spring, said first and second means extending from the respective ends of said coil spring.

13. The appliance of either of claims 1 or 2, wherein said spring means comprises a coil spring having at least one turn, said first and second means extending from the respective ends of said coil spring.

14. The appliance of either of claims 1 or 2, wherein said spring means comprises an elongated member interconnecting said first and second means and comprising a torsion spring means.

15. The appliance of claim 14, wherein said elongated member is made of wire.

16. The appliance of claim 1 wherein said first and second means each comprise an elongated member, said elongated members being interconnected along the longitudinal direction thereof, said elongated members being made of a resilient material exhibiting springiness, said interconnection along said longitudinal direction comprising said spring means when said elongated members are bent along said interconnection, the ends of said elongated members opposite said interconnection comprising said cooperating engagement means.

17. The appliance of claim 16, wherein said elongated members are substantially flat, rectangular members.

18. The appliance of either of claims 16 or 17, wherein said elongated members are made of spring metal.

19. The appliance of either of claims 16 or 17, wherein said elongated members are made of a plastic material.

20. The appliance of claim 16, wherein said first and second means comprise means for piercing gum tissue which is located between said pair of teeth.

21. The appliance of claim 1, wherein said first means comprises a first open-loop member and said second means comprises a second open-loop member, said first and second open-loop members being interconnected together and being made from a resilient material exhibiting springiness, said interconnected portions of said open-loop members comprising said spring means when said open-loop members are bent toward each other about said interconnection, the portions of said open loop members which are interconnected together comprising said cooperating engagement means.

22. The appliance of claim 21, wherein said first and second interconnected open-loop members form a generally figure-8 pattern.

23. The appliance of either of claims 21 or 22, wherein said first and second open-loop members are made of a spring metal material.

24. The appliance of claim 23, wherein said spring metal material is flat.

25. The appliance of either of claims 21 or 22, wherein said first and second open-loop members are made of plastic material.

26. The appliance of claim 21 wherein said first and second means comprise means for piercing gum tissue which is located between said pair of teeth.

27. The appliance of claim 1, further comprising third means adapted to be interposed into said space between said pair of teeth for bearing against said one opposing side surface; fourth means adapted to be interposed into said space for bearing against the other of said opposed side surfaces; and second spring means interconnecting said third and fourth means for biassing said third and fourth means away from each other and toward said opposed side surfaces of said pair of teeth to separate said opposed side surfaces.

28. The appliance of claim 27 wherein said first and third means bear against a common side surface of said pair of teeth, and said second and fourth means commonly bear against the other of said side surfaces.

29. The appliance of either of claims 27 or 28, wherein said first, second, third and fourth means each comprise means for piercing gum tissue which is located between said pair of teeth.

30. The appliance of either of claims 27 or 28, wherein each of said two spring means comprises an elongated coil spring.

31. The appliance of claim 30, wherein said elongated coil springs are engaged with each other.

32. The appliance of claim 30, wherein said elongated coil springs are nested one within the other.

33. The appliance of either of claims 1 or 2, wherein said spring means comprises a tortuously bent elongated member interconnecting said first and second means.

34. The appliance of claim 33, wherein said tortuously bent elongated member is generally V-shaped.

35. The appliance of claim 33, wherein said tortuously bent elongated member is generally W-shaped.

36. The appliance of either of claims 1 or 2, wherein both said first and second means extend substantially completely through said space between said pair of teeth.

37. The appliance of any one of claims 1, 7, 8, 16 or 21, wherein said cooperating engagement means on each of said first and second means extends substantially laterally of the respective tooth with which it is engaged.

38. The appliance of claim 37 wherein at least one of said first and second means comprises means for piercing gum tissue which is located between said pair of teeth and for locating said cooperating engagement means in said gum tissue.

39. The appliance of claim 38 wherein said piercing means comprises means for piercing said gum tissue in a direction substantially laterally of said teeth.

40. The appliance of claim 37 wherein both said first and second means comprises means for piercing gum tissue in a direction substantially laterally of said teeth.

41. The appliance of any one of claims 1, 7, 8, 16 or 21 wherein at least one of said first and second means comprises means for piercing gum tissue which is located between said pair of teeth and for locating said cooperating engagement means in said gum tissue.

42. The appliance of claim 41 wherein said piercing means comprises means for piercing said gum tissue in a direction substantially laterally of said teeth.

43. The appliance of claim 42 wherein both said first and second means comprises means for piercing gum tissue in a direction substantially laterally of said teeth.

44. The appliance of claim 11 wherein said first and second means comprise means for piercing gum tissue from opposite sides of said spring means and therefore, from opposite sides of said teeth.

45. The appliance of claim 20 wherein said first and second means have free ends remote from said interconnection, said free ends comprising said means for piercing gum tissue.

46. The appliance of claim 21 wherein at least one of said interconnected portions comprises said means for piercing said gum tissue, said piercing means being adapted to pierce said gum tissue in a direction substantially laterally of said teeth.

47. The appliance of any one of claims 1, 7, 8, 16, 21 or 27, wherein said spring means exhibits its springiness prior to insertion of said appliance between said pair of teeth.

* * * * *